(12) United States Patent
Brown (10) Patent No.: US 8,782,821 B2
(45) Date of Patent: Jul. 22, 2014

(54) PROTECTIVE FLEX EYEWEAR

(71) Applicant: Austin Brown, Hanover, PA (US)

(72) Inventor: Austin Brown, Hanover, PA (US)

(73) Assignee: WM. T. Burnett IP, LLP, Baltimore, MD (US)

( * ) Notice: Subject to any disclaimer, the term of this patent is extended or adjusted under 35 U.S.C. 154(b) by 0 days.

(21) Appl. No.: 13/740,731

(22) Filed: Jan. 14, 2013

(65) Prior Publication Data

US 2014/0026301 A1 Jan. 30, 2014

Related U.S. Application Data

(60) Provisional application No. 61/586,334, filed on Jan. 13, 2012.

(51) Int. Cl.
*A61F 9/02* (2006.01)

(52) U.S. Cl.
USPC .............................................................. 2/439

(58) Field of Classification Search
USPC ............... 2/9, 13, 15, 439, 445, 424, 446, 12, 2/450; 351/131, 132, 138
See application file for complete search history.

(56) References Cited

U.S. PATENT DOCUMENTS

| | | | | | |
|---|---|---|---|---|---|
| 2,197,973 | A | * | 4/1940 | Everett et al. | 2/13 |
| 2,233,698 | A | * | 3/1941 | Girouard | 2/206 |
| 2,519,561 | A | * | 8/1950 | Gillman et al. | 2/206 |
| 5,167,036 | A | * | 12/1992 | Daprato | 2/9 |
| 5,717,992 | A | * | 2/1998 | Tilghman | 2/9 |
| 7,416,299 | B2 | * | 8/2008 | Chen | 351/136 |
| 7,585,072 | B1 | * | 9/2009 | Wang-Lee | 351/138 |
| 8,327,466 | B2 | * | 12/2012 | Hahn et al. | 2/431 |

* cited by examiner

*Primary Examiner* — Tejash Patel
(74) *Attorney, Agent, or Firm* — Ober, Kaler, Grimes & Shriver; Royal W. Craig (57) ABSTRACT

Protective eyewear including a base, a floating protective wireframe (or lenses), an ear piece and a nose piece. The base can be substantially oval in shape, such that the base can surround the eyes of a user wearing the protective eyewear apparatus. The protective cage connects to the frame by snap fit or other means, and is otherwise spaced from and free-floating relative to the frame. This results in eyewear that is more comfortable to wear on a continuous basis and more reliable protection, at least meeting ASTM F 803-03 impact requirements.

34 Claims, 8 Drawing Sheets

PROTECTIVE FLEX EYEWEAR

CROSS-REFERENCE TO RELATED APPLICATION

This application claims the benefit under 35 U.S.C. §119 (e) of U.S. Provisional Application Ser. No. 61/586,334 filed Jan. 13, 2012, which is incorporated herein by reference.

BACKGROUND OF THE INVENTION

1. Field of the Invention

The present invention relates generally to protective eyewear, and more particularly, to a protective eyewear apparatus for sports such as women's lacrosse or field hockey.

2. Description of the Background

Protecting players from injury is a primary concern for any sport. Among the most vulnerable parts of the body are the head, face, and eyes. Thus, protective face masks and eyewear are common in sports such as baseball, hockey, football, racquetball, squash, and lacrosse. The sport of lacrosse uses a hard, heavy rubber ball that is thrown with considerable force and which can cause significant injury to unprotected eyes and faces. Most generally accepted rules for competitive lacrosse require a lacrosse ball made of solid rubber, between 7¾ and 8 inches in circumference (about 2½ inches in diameter), and between 5 and 5¼ ounces in weight. With the advances in lacrosse stick design, such lacrosse balls are routinely thrown at speeds in excess of seventy-five miles-per-hour such that impacts of the ball have caused countless bruises, numerous broken bones, and, in rare cases, even death. Indeed, in addition to the long-standing requirement of the rules for men's lacrosse that players wear helmets with face masks, protective eyewear is now mandatory according to the rules of women's lacrosse.

In general, manufacturers continually strive to improve the impact resistance of the protective eyewear they offer. However, improvements in the strength of the equipment often comes at the expense of comfort and dexterity as the equipment becomes more stiff, bulky, or obtrusive to the movement of the wearer. This discomfort can cause a player to choose to wear the equipment improperly or not at all, thereby defeating any improvement in the protection offered. Overall, protective eyewear should be comfortable to wear on a continuous basis and should provide ample protection in accordance with the applicable standards for its usage, including ASTM F 803-03 impact requirements. In providing comfort, the eyewear should be lightweight, flexible, and comfortable against the skin, and should provide adequate ventilation allowing the user to dissipate heat and moisture.

SUMMARY OF THE INVENTION

Accordingly, it is an object of the present invention to provide protective eyewear with a floating protective cage attached to a flex frame for greater comfort, stability and eye-protection.

In accordance with the above-described object, an embodiment of the present invention is a protective eyewear apparatus including a resiliently constructed frame for engaging the head of the wearer and a protective element such as a wire cage or a lens for shielding the face or eyes. The frame may be a partial oval in shape, such that the base can surround the head and eyes of a user wearing the protective eyewear apparatus and remain securely engaged to the head during play. The frame includes temple arms extending over the ears of the wearer and joined across the face by a brow piece positioned substantially at the brow line. A nasal bridge piece extends down from the brow piece over the upper part of the wearer's nose and may continue to a flared nose piece covering a lower portion of the nose. The distal ends of the temple arms may be joined by a strap extending behind the head to further secure the eyewear in place. The protective element may be provided in the form of a unitary wire cage having an upper bar and a lower bar joined at the sides in a continuous loop circumscribing a viewing aperture of the frame. A center plate is attached at least to the upper bar and extends toward the lower bar, preferably straddling the two and also being attached to the lower bar. The center plate serves to removably connect the protective element to the frame such as, e.g., by a snap fit or other means. Importantly, only the center portion of the upper bar (and optionally the lower bar) are anchored to the nasal bridge piece of the frame by the plate, and the remainder of the protective element is suspended away from the frame so as to float over it in its normal-unbiased position, thereby permitting the resilient frame to freely flex independently of the protective element and better accommodate a variety of different head shapes and sizes.

The resilient frame is defined by a contact area in the region surrounding the viewing aperture to engage the floating protective element when it is displaced from its ordinary position during play (such as by contact with an external object such as a lacrosse ball or the stick of another player). The contact area may have surface features such as raised portions to ensure first contact with the displaced protective element. The contact area may also comprise an annular channel, groove or recess in which the protective element is received, thereby seating the protective element and resisting lateral motion until it returns to its ordinary floating position.

Optionally, the frame includes generally arcuate cheek members protruding downward on opposing sides of the brow piece for cheek protection. The upper bar is connected to the frame via the center plate near the middle of the base proximate a user's nose and in two other locations approximately above a user's eyes. The upper bar is disposed closer to the forehead base member than the lower bar.

A further embodiment of the present invention includes a compressible layer disposed on at least a portion of the frame, for example, in areas at which the base is intended to contact a user's skin. In one implementation, a first compressible layer is disposed on the brow piece and a second compressible layer is disposed on the cheek member. The compressible layer can be, for example, a foam (e.g., open or closed cell) or an elastomer. On the frame members, the compressible layer is generally in contact with the user's face and provides a compressible outer surface that conforms comfortably to the contours of a user's face for comfort and secure engagement. In a further embodiment, the compressible material may be provided with a textured surface in which raised portions of the textured surface contacting a user's skin while depressed portions hold perspiration. The compressible layer may be covered by a performance fabric to control and dissipate moisture/perspiration.

The protective eyewear described herein is comfortable to wear on a continuous basis and provides ample protection at least meeting ASTM F 803-03 impact requirements.

The above and other objects, features and advantages of the present invention will become readily apparent from the following detailed description thereof which is to be read in connection with the accompanying drawings.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENTS

The present invention is a protective eyewear including a resilient frame preferably secured to the wearer's head by an elastic strap and a floating protective element comprising a wireframe cage or lens attached to the frame. The resilient frame may be formed of impact-resistant plastic such as nylon or polycarbonate to both permit, according to the present invention, proper fit of the frame on a wide range of head/face shapes and sizes and to distribute and dissipate impact forces during play. The frame preferably comprises opposing temple portions extending on either side of the head and joined by a brow piece or portion across the brow of the wearer, generally in the manner of eyeglasses and other protective eyewear. The frame is preferably arched or arcuate so as to wrap around the wearer's brow to conform to the head above the eyes, and may be formed in a partial oval shape in this regard. The protective element is joined to the frame centrally at the brow piece in such a way as to permit and control flexing of both the frame and the cage, as will be described. To achieve one or more of the goals of the invention the protective element connects to the frame by snap fit or other means and is spaced away from and free-floating relative to the frame. This results in eyewear that is more comfortable to wear on a long-term basis and which affords improved impact protection, at least meeting ASTM F 803-03 impact requirements.

Figure 1:
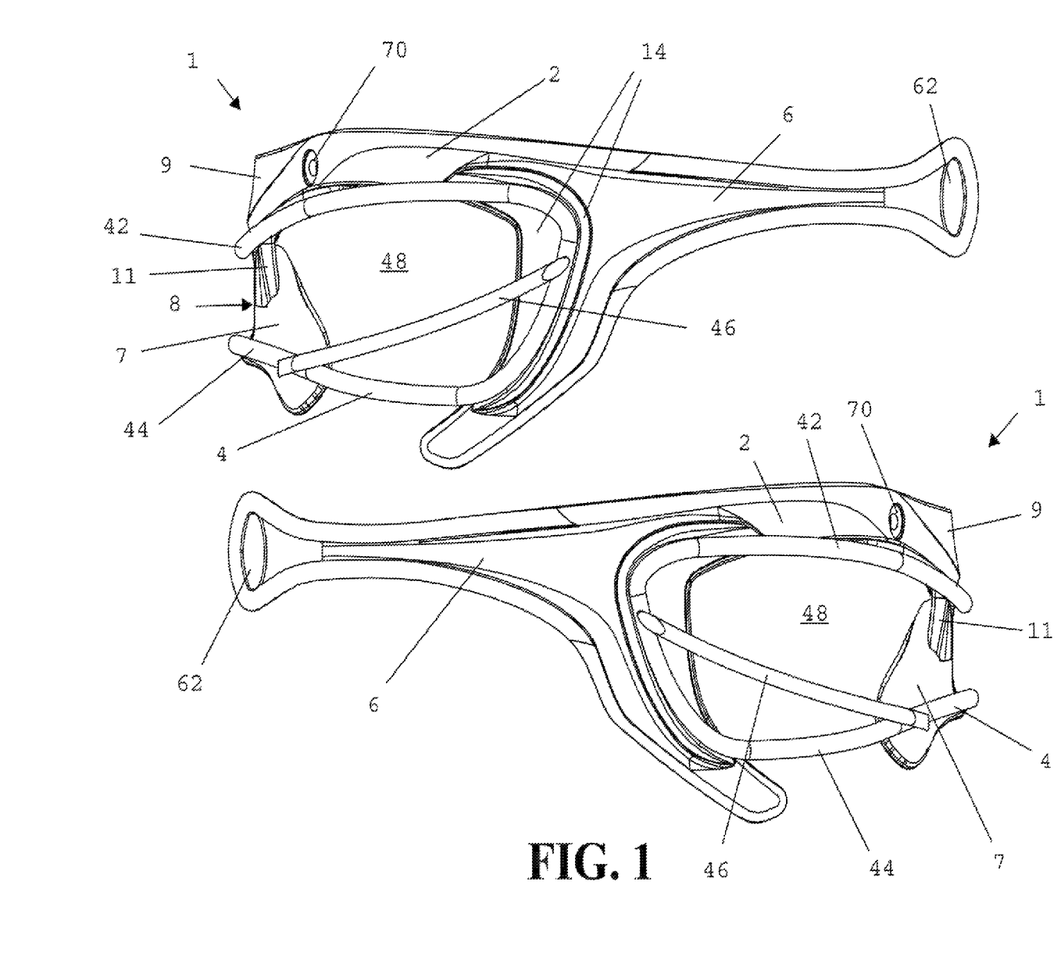
FIG. 1 is a side view of protective eyewear according to the present invention.
Figure 2:
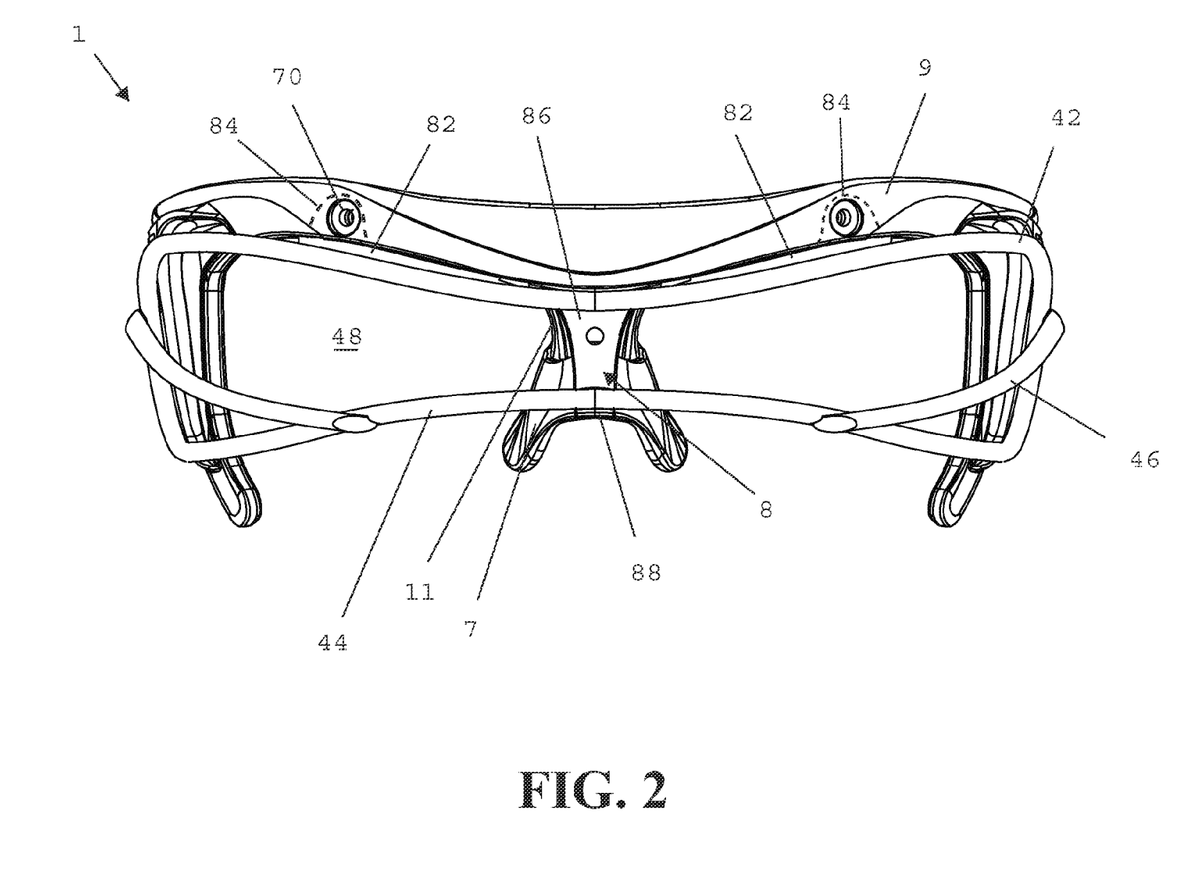
FIG. 2 is a front view of protective eyewear according to the present invention.
Figure 3:
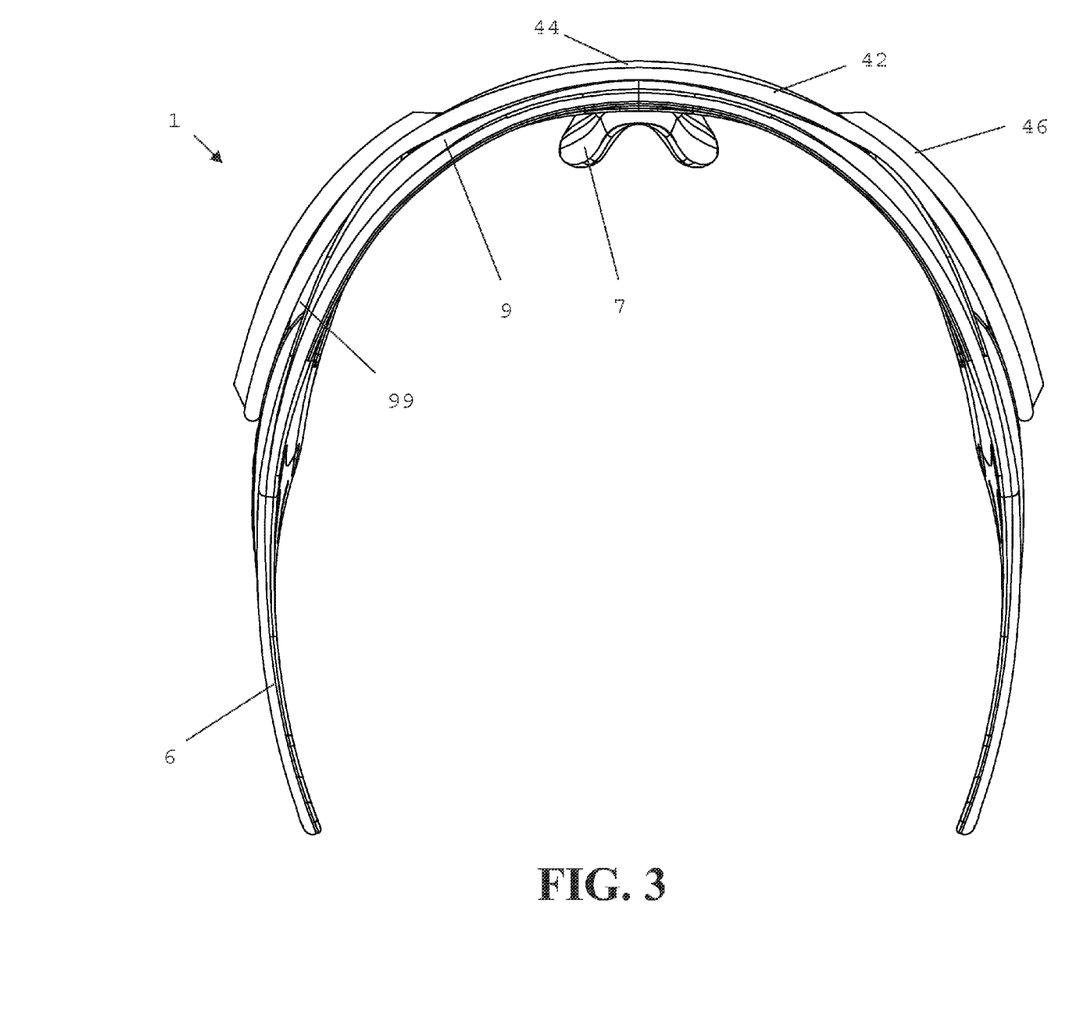
FIG. 3 is a top view of protective eyewear according to the present invention.
Figure 4:
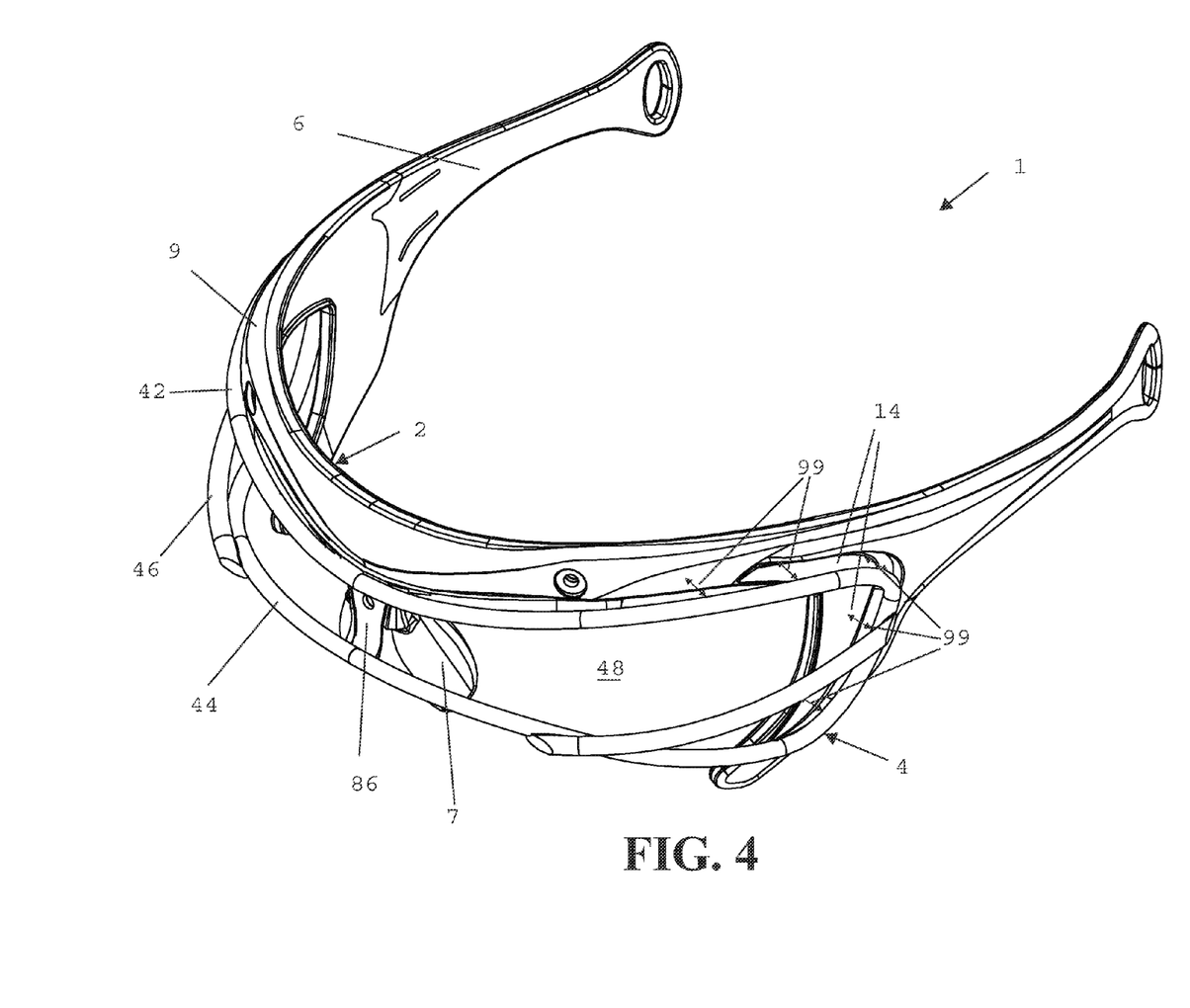
FIG. 4 is a three-quarters front perspective view of protective eyewear according to the present invention from above.

With combined reference to FIGS. 1-8, an embodiment of the protective eyewear 1 of the present invention is depicted including resilient frame 2 and a protective element in the form of a wire frame cage 4. The frame 2 includes unitary temple portions 6 which straddle and engage opposing sides of the head of the wearer above the ears and which are joined by a brow piece 9 that substantially spans the brow of a wearer above the eyes. As seen in FIG. 2, a nasal bridge portion 11 protrudes down from the brow portion 9 over the upper part of the wearer's nose and adjoins a flared nose piece 7 formed to cover a lower portion of the nose. Referring back to FIG. 1, the opposing temple portions 6 support the flex frame 2 on the head at and above the ears and may be joined by a hinge or integrally formed with the brow portion 9 in a continuous curve so as to wrap around the head of the wearer, spanning the brow above the eyes. An oval or oblong curvature of the flex frame 2 around the head serves to more securely engage the frame 2 to the head. Two or more holes 70 or other means of attachment may optionally be positioned laterally within the brow portion 9 for supplemental (three-point) attachment of the cage 4 (as will be described). The distal ends 62 of the temple portions 6 may be formed with a circular hole or slot 62 within which to secure the ends of a band or strap (not shown), preferably elastic, to wrap around the head of the wearer and more securely retain the flex frame 2 on the head.

The protective element of the illustrated embodiment is a unitary wire-frame cage 4 contiguously formed with an upper bar 42 and a lower bar 44 joined at the sides to define a viewing aperture 48. The cage 4 is contoured along a horizontal plane (as best seen from above in FIG. 3) to conform to the frame 2 and may also be contoured vertically (as seen from the front in FIG. 2). One or more diagonal reinforcing struts 46 may be provided to reinforce the protective cage 4. The upper and lower bars 42, 44 generally converge to closest proximity at their centers and a center plate 8 is attached rearwardly of the upper bar 42 and protrudes at least partially toward the lower bar 44. Center plate 8 may extend fully to the lower bar 44 and be attached rearwardly thereto (as seen in FIG. 2). The center plate 8 may be of the same or different material as the cage 4 and may be welded, integrally formed or fixedly attached by other suitable means.

Importantly, the upper bar 42 of the cage 4 is joined centrally to the brow portion 9 of the frame 2, in this instance by affixing center plate 8 to the nasal bridge portion 11 protruding down from the brow portion 9 (FIG. 2), leaving the sides of the cage 4 free from attachment to the frame 2 so as to be free to "float" over the frame. Holes 70 provide optional attachment points to form a three-point attachment if desired, which more securely affixes the cage 4 but compromises some degree of float. Toward this end the center plate 8 may optionally be formed as an elongate T-shaped member having struts 82 extending laterally from the vertical element 86 to holes 70. The struts 82 are attached to and conform to the contour of the upper bar 42, running along the upper bar to upwardly-protruding flanges 84 (see dotted lines in FIG. 2) secured behind or, preferably, within the frame 2 at holes 70. The upper struts 82 extend centrally along the upper bar 42 over approximately the central third of the upper bar 42 before terminating at the two offset upwardly-protruding flanges 84 at the distal ends. The flanges 84 are formed with holes for anchoring to the holes 70 of flex frame 2 by rivets, snaps, screws or the like. As in FIG. 2, whether or not a T-shaped center plate is used, the vertical element 86 of the center plate 8 may extend down to an angled lip or trough 88 that serves as a yoke to grip or engage the underside of lower bar 44. The vertical element 86 of the center plate 8 is likewise defined by a single hole for anchoring a snap, screw or other attachment to the nasal bridge 11 and/or nose piece 7.

One skilled in the art should understand that the arms 82 and flanges 84 of the T-shaped center plate 8 need not be attached to the cage 4 along their entire lengths, but may be attached centrally and progressively offset outwardly along upper bar 42 to vary the degree of float. The flanges 84 may be engaged to the front of the brow piece 9 at holes 70, the back of the brow piece, or inserted within slots formed in the underside of the brow piece 9. In addition, the flanges 84 may be formed as separate components, distinct from center plate 8 and attached directly to the upper bar 42 in the positions shown. The attachment points need not be confined to a T-shaped three-point attachment as shown in FIG. 2. Rather, an embodiment may be provided in which all of the characteristics of the T-shaped center plate 8 attachment are offered by one or more alternate elements that still allow independent flexibility of the outer portions of the protective element 4. For example, the cage 4 or other protective element may be directly affixed to or integrated with the central portion of the central brow area 9 and/or nasal bridge area 11 of the flex frame 2.

The above-described configuration makes it possible to attach the protective cage 4 to frame 2 at multiple attachment points. Although more connection points are possible, three connection points are preferred to provide a triangulated attachment wherein the position of the connection point or points relative to the width of the cage 4 (in conjunction with the other elements and materials of the invention) more so than the number that enables the benefits of the invention. Projection of the protective element in front of the frame, be it wire cage 4, lens or otherwise, increases the inertial moment of the frame/protective element assembly as the connection points are moved toward the lateral margins. If, as in the present invention, the connection point(s) are maintained within preferably the middle third, and more preferably the middle quarter of the protective element, such that the frame and protective element are permitted to move largely independently of each other to achieve the desire result of the invention. This is so even where the frame and protective element are maintained in contact with one another outside the connection region.

Figure 5:
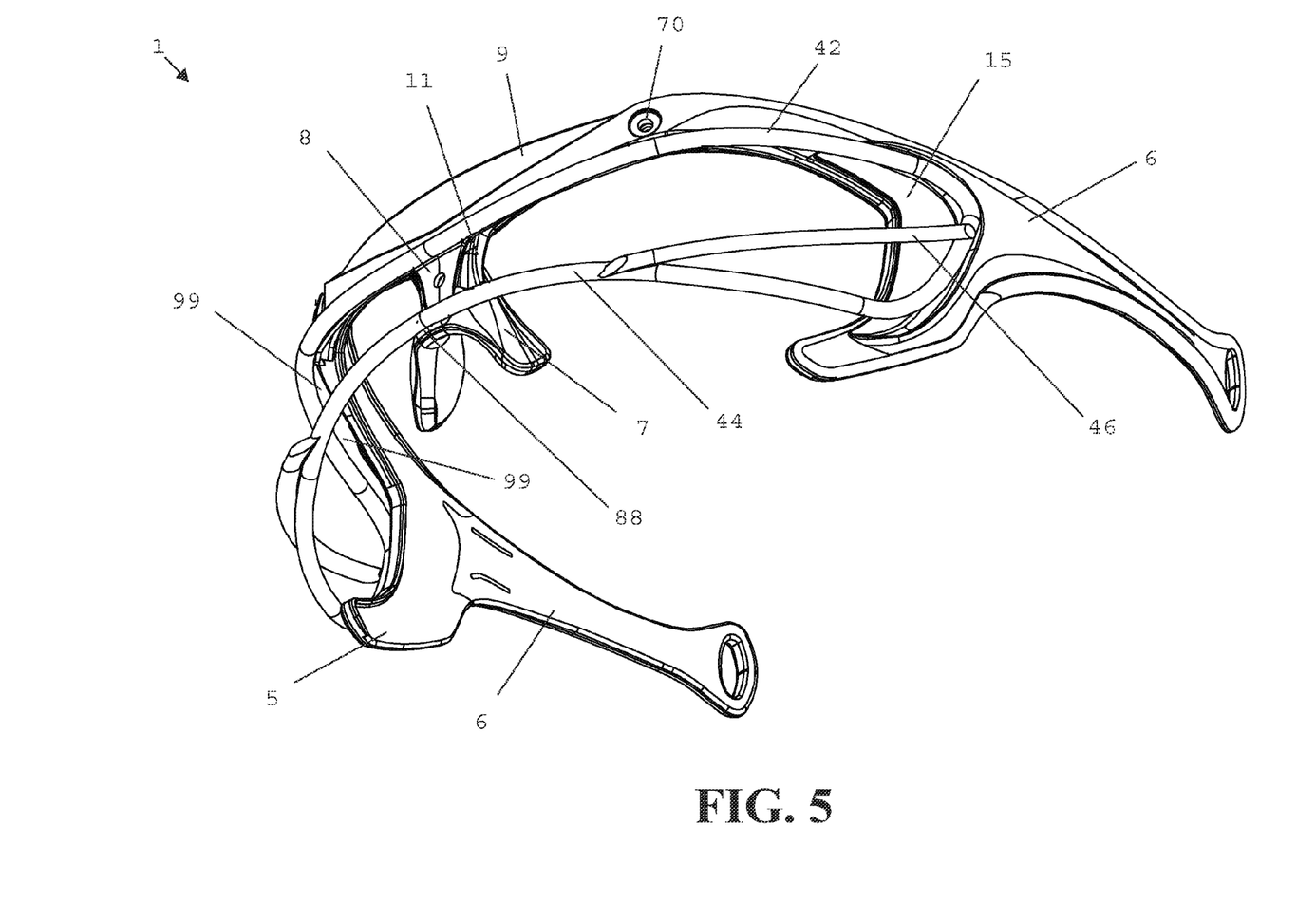
FIG. 5 is a three-quarters front perspective view of protective eyewear according to the present invention from below.
Figure 6:
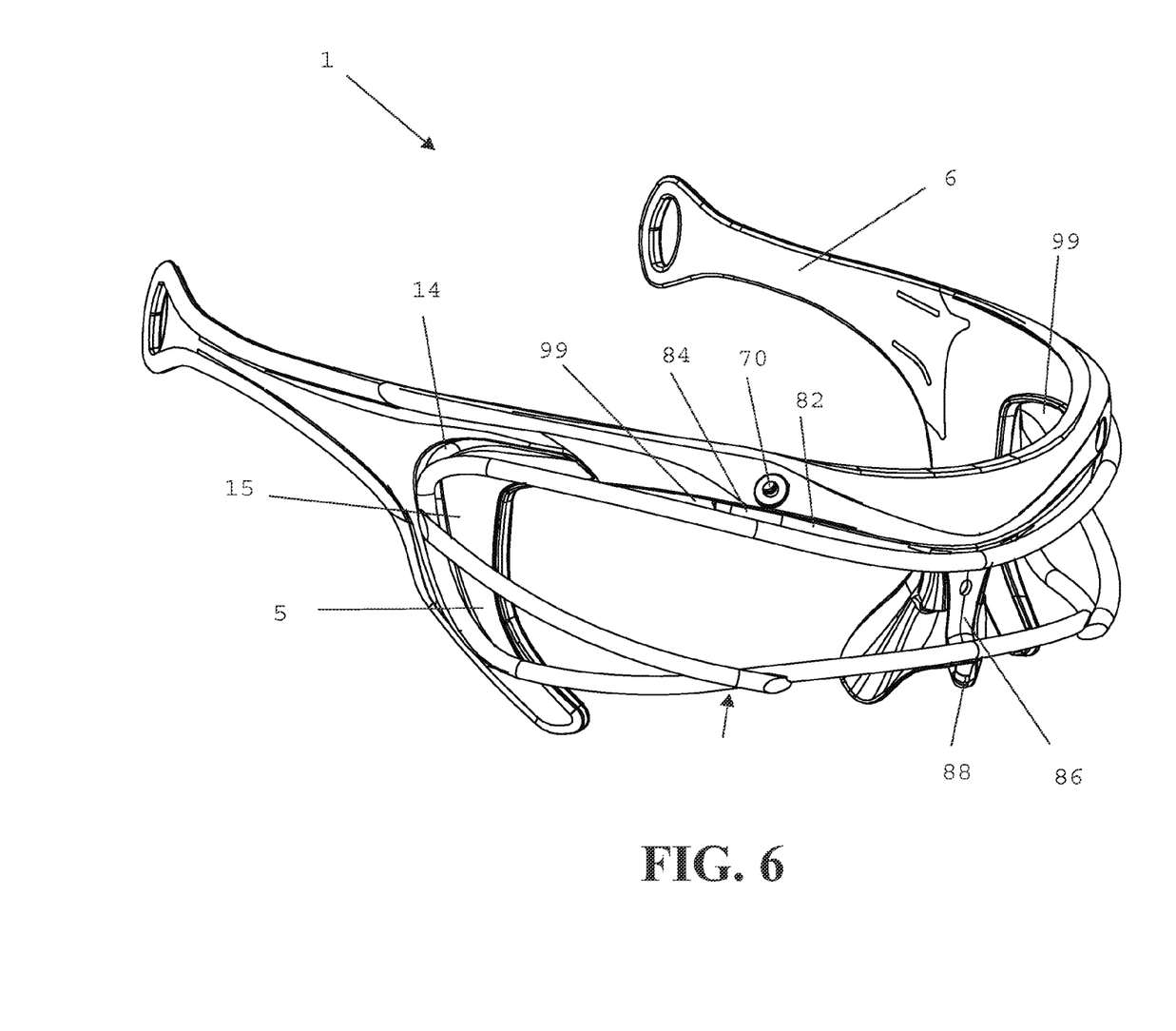
FIG. 6 is a three-quarters front perspective view of protective eyewear according to the present invention from above.
Figure 7:
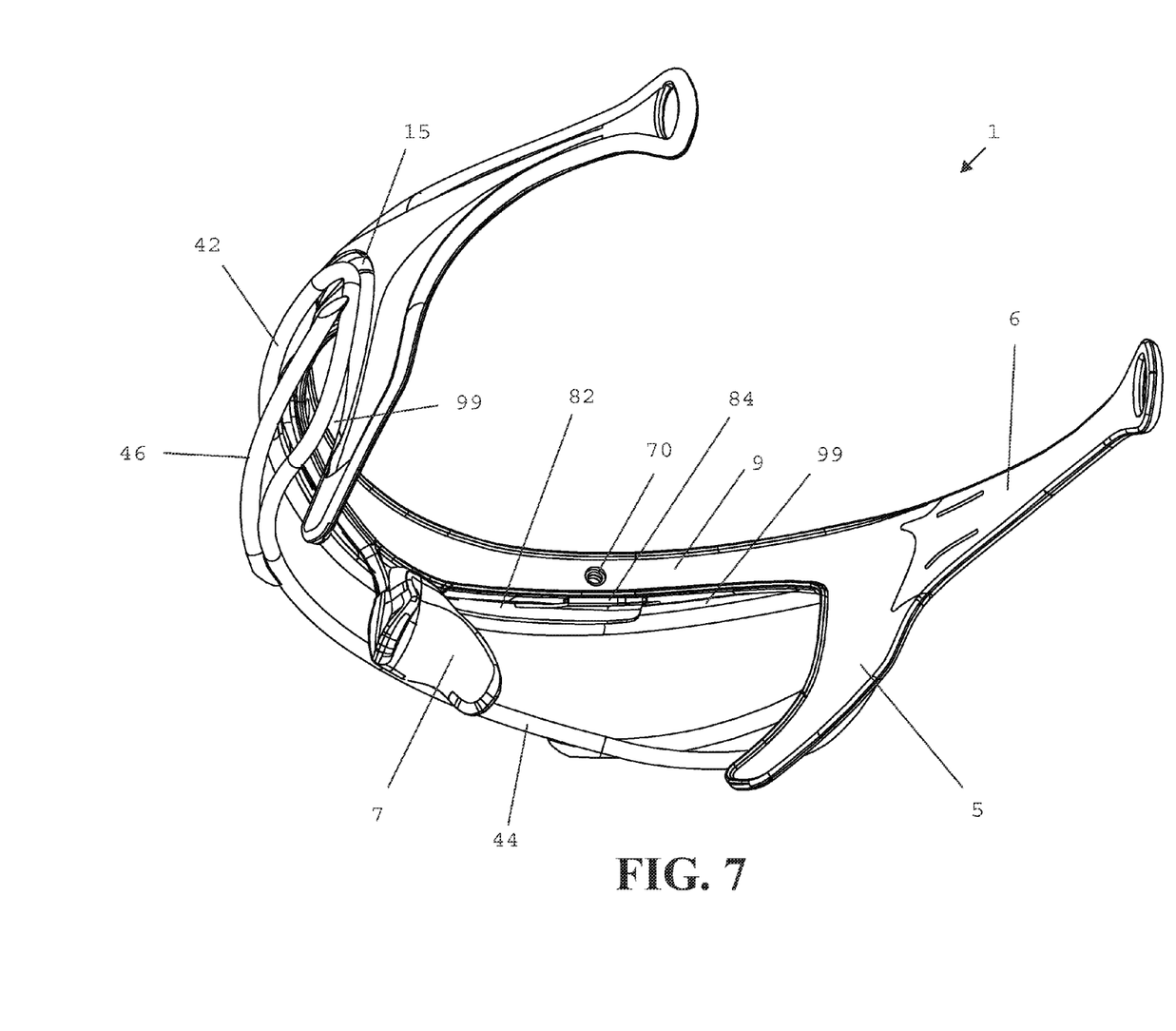
FIG. 7 is a three-quarters rear perspective view of protective eyewear according to the present invention from below.
Figure 8:
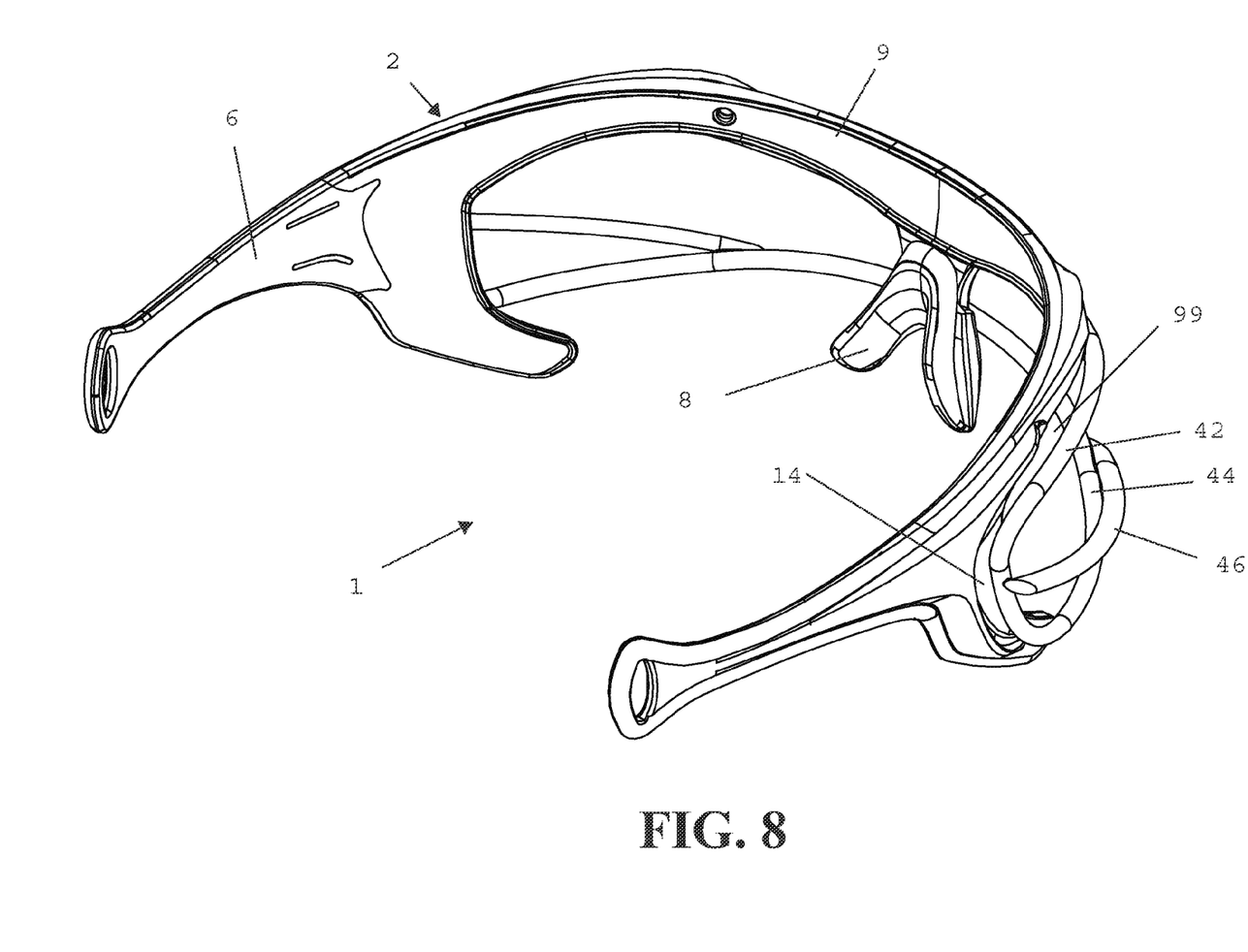
FIG. 8 is a three-quarters rear perspective view of protective eyewear according to the present invention from above.

As perhaps best seen in FIG. 5, 7 or 8, the laterally distal portions of the wire frame 4 (laterally outside or beyond the connection points between the cage 4 and flex frame 2 (i.e., the flanges 84 in the illustrated embodiment) may additionally be maintained away from the flex frame 2 by a gap 99 in order to provide enhanced energy dissipative functionality. That is, in their ordinary position, the lateral portions of the cage 4 or other protective element are not in contract with the flex frame 2, but are spaced therefrom by gap 99 best seen in FIG. 4. The size of the gap 99 will be selected based on the modulus of elasticity and the bending stiffness of the cage 4 and frame 2 elements. After allowing for sufficient expansion in the frame diameter to accommodate the wearer's head, the gap 99 should be chosen based on the amount of force permitted to be applied to the cage 4 (such as by a lacrosse ball impact) before the cage strain closes the gap 99 and the cage engages the frame 2. The gap 99 may be within a range of 0 mm-20 mm, and is most preferably approximately 5 mm in order to permit and accommodate flexing of both the frame 2 and cage 4.

With or without the T-shaped configuration of center plate 8, the lower bar 44 is not connected to the flex frame 2 but rather only connects via the vertical element 86 of the center plate 8 to the brow portion 9 of the frame 2. In this embodiment, the frame-cage attachment by way of the center plate 8 is the basis for the flexibility in the overall eyewear 1. Specifically, no more than the central one-third length of the upper bar 42 of cage 4 is secured to flex frame 2 by way of center plate 8, leaving the entire remainder of the cage 4 free and floating. Moreover, no more than the central brow portion 9 of the flex frame 2 is encumbered (being attached at two points roughly above the eyes), allowing the majority of the flex frame 2 free to flex independently of the rigid cage 4. This helps make the protective eyewear 1 adaptable to a wide range of face widths and also allows the cage to absorb the energy of impacts during play.

In use, the frame 2 is placed on the head of the wearer in the manner of eyeglasses. Where a wearer has a relatively wider head and face, the frame 2 is permitted to flex in the outer portions of the brow portion 9 and in the temple portions 6 beyond the as-molded or as-constructed size and shape to accommodate the head of the wearer. This will tend to diminish the gap 99 and should be accounted for in selecting the gap size. Where a wearer has a relatively narrow head and face, a back-of-head strap can be tightened such that the frame 2 flexes inward to form a snug fit on the head of the wearer. This, conversely, will increase the size of the gap 99 and should also be accounted for when selecting the gap size. Under either condition, the construction and material selection of the frame 2 allows flexure and the gap between the rigid cage 4 and "floating" frame 2 ensures that the cage does not impede flexure. Consequently, a single sized protective eyewear can accommodate faces as wide or as narrow as (approximately) the $90^{th}$ percentile. The as-molded or as-constructed (i.e., "at-rest" or "un-flexed") frame 2 is preferably sized at the midrange face size to accommodate the average wearer.

Allowing the cage 4 to "float" about the frame 2, serves not only to allow flexure of the frame 2 to accommodate wearers of differing sizes, but also to disperse, dissipate and absorb impact forces on the upper, lower and reinforcing bars 42, 44, 46. As described, when impacted during play by a hard rubber lacrosse ball or otherwise, the floating cage 4 may flex toward the frame 2 at the lateral ends through the air gap 99, thereby dissipating the energy of the impact, protecting the wearer and helping to prevent the protective eyewear from becoming dislodged from the face or head of the wearer. Slight impacts may not deflect the cage 4 sufficiently to entirely close the air gap 99 and thereby come into contact with the frame 2, but more severe or energetic blows may do so and the frame 2 is constructed to advantageously handle this eventuality.

The present invention improves the ability to channel or redistribute impact forces to the cage 4 in a controlled manner. Several optional design features illustrate this. With continued reference to the figures and with particular reference to FIGS. 1, 4 and 6, the preferred embodiment of the protective eyewear 1 includes a bottom-out or bounding zone 14 formed in the frame 2 to provide a bearing surface and/or cushioning action for the floating cage 4 should it contact the frame 2. The temple portions 6 are preferably formed with cheek extensions 5 protruding downward along the side and toward the front of the wearer's face in front of the ears. The cheek extensions 5 preferably extend to and over the prominence of the cheekbone (zygomatic bone) and are likewise formed with surface features that provide an integrated bounding zone 14. The side extensions 5 also preferably extend down past the bottom of the rigid cage 4 (i.e., the lower extremity of lower bar 44). This extends the bounding zone 14 around the sides of cage 4 and frame 2 of the protective eyewear 1, providing greater stability to the cage 4 when deflected, and further protecting the wearer's face from side blows. The lateral portions of the cage 4 are spaced directly in advance of and thus float over the cushioning bounding zone 14 such that impacts to the cage 4 press it against this zone where the energy from contact can be absorbed.

As seen in FIG. 5, some or all of the bounding zone 14 in frame 2 and extensions 5 may be formed with surface features such as a furrow, groove or channel 15 cooperatively aligned with the shape of the cage 4 so that the cage 4 is received and seated within the channel 15 upon contact with the frame 2. This configuration limits lateral motion or displacement of the cage 4 relative to the frame 2 due to impact. This self-aligning surface feature 15 prevents misalignment of the cage with the frame due to energetic impacts that might otherwise overpower the floating attachment means.

As a matter of design choice, the bounding zone 14 may be hard and smooth with a low coefficient of friction allowing the cage 4 to spread upon impact. In this case, the arched shape of the cage 4 causes it to act like a leaf-spring and dampens impact. Alternatively, the surface features 15 may be a high coefficient of friction material to resist lateral movement of the cage 4 relative to the frame 2 upon impact. In this case the high coefficient of friction provides traction for the rigid cage 4, such that the cage 4 and flex frame 2 become locked in place at the moment of impact. This tends to minimize deflection of the ball.

Further energy absorption and distribution may be accomplished by constructing the frame 2 and cheek extensions 5 with an applied/overmolded layer of deformable rubber or other cushioning material. Overmolded cushions greatly dampen the contact between the rigid cage 4 and flex frame 2 when force of any kind is applied to the protective eyewear 1.

The recessed bounding zone 14 may further include slightly built up or raised areas, such as ribs or pads, evenly spaced around its perimeter. Such raised areas surround the cage 4 to ensure first-contact with the deflected cage 4, channeling the impact forces through the raised areas into the frame 2, and thereby increasing the dampening effect.

The present invention contemplates an ability to easily remove and replace the cage 4 from the frame 2 and replace it with another cage or shielding element to accommodate the preferences of the wearer, the requirements of an alternate sport or differing requirements between leagues of the same sport. The above-described T-shaped center plate 8 is one means by which to facilitate such interchangeable eye protection options and it is envisioned that plate 8 may be removably or semi-permanently attached to allow a varying array of eye protection options and materials. For example, wearers may swap out their cage 4 for another rigid cage design to switch from lacrosse to field hockey, or switch a wire cage to clear lens protection, or the like. Alternatively, a different connection method may avoid the need for center plate 8 such that interchangeable cage designs or lenses may directly engage the flex frame 2 in the disclosed floating configuration, provided there is still a degree of separation from flex frame 2 allowing flexibility of the outer portions of the flex frame 2.

The present invention may further include padding disposed on at least a portion of the inside surface of the frame 2 in areas in which the frame 2 is intended or expected to contact a wearer's skin, e.g., within the bounding zone 14. For example, padding may be disposed along the forehead and at the cheek bones. The padding may be any suitable compressible layer such as, for example, an open or closed cell foam, an elastomer or a knit, woven or non-woven fabric. An elastomer can be overmolded or adhered onto the brow/temples/extensions of the eyewear 1. If desired, the padding may have a textured surface, with raised portions of the textured surface contacting a user's skin and depressed portions of the textured surface holding perspiration. A layer of performance fabric over the compressible padding layer may be provided. Performance fabric can be disposed over the portions of the eyewear 1 that contact the user's skin, such as locations at which the eyewear contacts the user's forehead and cheeks.

One skilled in the art should readily understand that manufacturing methods and materials may vary. For example, the protective cage 4 need not be a separately-manufactured wireframe component assembled to the flex frame 2, but instead can be integrally-molded or otherwise manufactured as a unified part with the rest of the protective eyewear 1. In all such cases, the flex protective eyewear 1 with floating protective cage 4 attached to a flex frame 2 increases comfort, stability and quality of vision.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. Protective sports eyewear, comprising
a resilient frame configured to extend around a portion of the head of a player at said player's brow, said frame having opposing temple portions extending on either side of said head and joined by a brow piece spanning said player's brow;
a protective element configured for cooperative conformance with said frame and comprising a middle portion affixed to said frame, said protective element further comprising opposing side portions extending laterally from said middle portion toward said temple portions, said side portions being un-affixed to said frame so as to remain free-floating relative to said frame, said middle portion and side portions together defining a viewing aperture surrounding both eyes of said player.

2. The eyewear of claim 1, wherein said temple portions are integrally formed with said brow piece.

3. The eyewear of claim 1, wherein said temple portions are affixed to said brow piece by a hinge.

4. The eyewear of claim 1, wherein said middle portion is affixed to said brow piece of said frame.

5. The eyewear of claim 1, wherein said frame further comprises a nasal bridge portion protruding downward from said brow piece.

6. The eyewear of claim 5, further comprising a flared nose protector attached to said nasal bridge portion.

7. The eyewear of claim 5, wherein said middle portion is affixed to said nasal bridge portion of said frame.

8. The eyewear of claim 1, wherein said middle portion comprises a middle third of said protective element.

9. The eyewear of claim 1, wherein said side portions are spaced from said frame by a predetermined gap.

10. The eyewear of claim 9, wherein said gap is within a range from 0 mm-20 mm.

11. The eyewear of claim 10, wherein said gap is approximately 5 mm.

12. The eyewear of claim 1, wherein said protective element comprises a wire cage.

13. The eyewear of claim 1, wherein said protective element is a transparent lens.

14. The eyewear of claim 1, further comprising a center plate affixed to said protective element at a first point positioned within said center portion and affixed to said frame at a second point.

15. The eyewear of claim 14, wherein said second point is on said brow piece.

16. The eyewear of claim 15, wherein said center plate further comprises opposing lateral extensions affixed to said brow portion at a third point and a fourth point to form a triangulated attachment.

17. The eyewear of claim 16, wherein said center plate comprises a T-shaped member.

18. The eyewear of claim 14, wherein said frame further comprises a nasal bridge portion protruding downward from said brow piece and wherein said second point is on said nasal bridge portion.

19. The eyewear of claim 1, wherein a surface of said resilient frame further comprises a grooved bounding zone cooperatively aligned with said protective element.

20. The eyewear of claim 19, wherein said bounding zone comprises a confined area for seating said protective element.

21. The eyewear of claim 20, further comprising a deformable pad in said bounding zone configured to deform on contact by said protective element.

22. The eyewear of claim 20, further comprising a raised area in said bounding zone configured to make first contact with said protective element.

23. The eyewear of claim 1, wherein said temple portions each further comprises a cheek protrusion extending downward to and over a portion of the cheekbones of said wearer.

24. The eyewear of claim 23, wherein a surface of said resilient frame further comprises a defined bounding zone cooperatively aligned with said protective element and extending across both cheek portions and at least a portion of said brow portion.

25. A method of affixing a protective element to a resilient frame of a protective eyewear, comprising the steps of:
   providing a resilient frame having opposing temple portions configured to extend on either side of a wearer's head and joined by a brow piece spanning said wearer's brow;
   providing a protective element configured for cooperative conformance with said frame and comprising a middle portion occupying the middle third of said protective element and flanked by opposing side portions extending laterally from said middle portion,
   affixing said middle portion of said protective element to said resilient frame while maintaining said opposing side portions in an un-affixed state relative to said frame such that the opposing side portions of said protective element remain free-floating relative to said frame;
   whereby said temple portions and said brow piece are permitted to flex independently of the side portions of said protective element in order to accommodate said wearer's head shape or size.

26. The method of claim 25, further comprising the step of affixing a back-of-head strap to a distal end of said temple portions.

27. The method of claim 25, further comprising the step of providing a T-shaped mounting plate for affixing said protective element to said brow piece, said T-shaped mounting plate comprising a horizontal strut for receiving an upper edge of said middle portion of said protective element, a flange at each distal end of said horizontal strut for attachment to said brow portion, and a vertical strut for receiving a lower edge of said middle portion of said protective element.

28. The method of claim 25, further comprising the step of providing a gap between said opposing side portions of said protective element and said frame.

29. The method of claim 28, further comprising the step of providing a bounding zone on at least a portion of a surface of said frame for engaging at least a portion of said opposing side portions of said protective element when said protective element closes said gap.

30. Protective sports eyewear, comprising:
   an eyeglass frame formed from a resilient material and having opposing temple arms extending on either side of the head of a wearer and joined to an arched brow piece spanning said wearer's brow;
   a protective element defining a viewing aperture;
   an intermediate attachment bracket for attaching said protective element to said eyeglass frame, said attachment bracket being fixedly attached to a central portion of said protective element leaving the remaining portions of said protective element unattached and free to float on either side of said attachment bracket in relative proximity to said eyeglass frame at a predetermined spacing between said protective element and said eyeglass frame when so attached, and;
   a nose piece attached to said bracket.

31. The eyewear of claim 30, wherein said protective element comprises a wire frame.

32. The eyewear of claim 30, wherein said predetermined spacing is within a range from 0 mm-20 mm.

33. The eyewear of claim 32, wherein said predetermined spacing is approximately 5 mm.

34. The eyewear of claim 30 further comprising
   an extension descending from each of said temple portions of said frame to and over a portion of the cheek bones of said wearer, and
   a bounding zone comprising one or more surface features extending along at least a portion of said brow piece and said extensions for engaging said wire frame when said predetermined spacing is temporarily eliminated.

* * * * *